United States Patent [19]

Bohl et al.

[11] 4,381,153

[45] Apr. 26, 1983

[54] OPACITY MONITOR

[75] Inventors: Thomas L. Bohl, Madison; George R. Hall, Jr., Euclid; Sharon L. Zimmerlin, Chagrin Falls, all of Ohio

[73] Assignee: The Babcock & Wilcox Company, New Orleans, La.

[21] Appl. No.: 182,203

[22] Filed: Aug. 28, 1980

[51] Int. Cl.³ .............................................. G01N 21/01
[52] U.S. Cl. .................................... 356/437; 250/236
[58] Field of Search .............................. 356/436–439, 356/325, 323; 250/573, 575, 236

[56] References Cited

U.S. PATENT DOCUMENTS 1,996,233  4/1935  Darrah .............................. 250/573

Primary Examiner—Bruce Y. Arnold

Attorney, Agent, or Firm—James A. Hudak; Vytas R. Matas; Robert J. Edwards

[57] ABSTRACT

An opacity monitor (10) including a light source (12) mounted on one side of a duct (14), and a detector (16) mounted on the opposite side of the duct is disclosed. The light source (12) and the detector (16) are rotated by motor means (26, 36), respectively, between a first position aligned with each other along an open light path defined across the duct (14) and a second position aligned with each other on opposite sides of a calibration tube (18) extending across the duct (14). Shutters (28, 38) rotate with the light source (12) and the detector (16), respectively, and are aligned with the calibration tube (18) when the light source (12) and the detector (16) are aligned with the open light path, and vice versa.

5 Claims, 2 Drawing Figures

4,381,153

OPACITY MONITOR

TECHNICAL FIELD

The present invention relates generally to opacity monitors, and more particularly to an opacity monitor which includes a permanent calibration pipe.

BACKGROUND ART

Opacity monitors are used in power generating plants and in other applications wherein exhaust gases from some form of industrial process can release pollutants into the atmosphere. A typical opacity monitor includes a transmissometer which measures the transmittance of light through an optical medium to provide an indication of the opacity of exhaust gases flowing through an exhaust stack or duct; the opacity of the exhaust gas indicating the amount of particulate matter or pollutants in the exhaust gas.

One known form of monitor consists of an optical transceiver unit mounted on one side of a duct, and a reflector unit mounted on the other side. The transceiver unit contains a light source, a detector, and electronic circuitry, whereas the reflector unit houses a passive retroreflector. Another form of monitor uses a source on one side of a duct and a detector on the other side, the exhaust gas passing by a slotted pipe extending across the duct between the source and the detector.

In any type of opacity monitor, the monitoring system must be periodically calibrated to obtain a true zero reading and an accurate upscale range for an opacity reference. In the type of monitoring utilizing a source and a detector on opposite sides of the duct, zero calibration is obtained by manually inserting a calibration tube through the duct or by stopping the process while calibration is being effected. The calibration tube is awkward to handle and requires an operator to go to the monitoring location to effect calibration. Alternately, it may not be possible or practical to periodically stop the process for calibration. In the retroreflective system, calibration involves mechanically moving a mirror outside the source/detector housing window. Inherent disadvantages of this system include alignment problems in positioning the mirror, and the exposure of moving parts to a hostile environment.

Because of the foregoing, it has become desirable to develop an opacity monitor that can be readily and easily calibrated without stopping the process being monitored.

SUMMARY OF THE INVENTION

The present invention solves the aforementioned problems associated with the prior art as well as other problems by providing an opacity monitor with a permanent calibration pipe associated therewith. More specifically, the present invention provides two paths across the exhaust duct; one path for measuring the opacity of the gas passing through the duct and the other path for calibrating the monitor. The monitor comprises a transmissometer which includes a light source mounted on one side of the exhaust duct; a detector mounted on the other side of the duct, with a light path extending across the duct; and a calibration pipe, closed to the gas in the duct, extending through the duct. The light source and the detector are rotatable between first positions wherein they are aligned across the light path, and second positions wherein they are aligned across the calibration pipe. Shutters are also rotatable with the light source and the detector and oppositely positioned therefrom so that the shutters close off the calibration pipe when a measurement is being taken across the light path and close off the light path when calibration is being effected. Rotation of the light source and the detector can be effected by servo motors, rotary solenoids, or the like, and can be effected remotely so that there is no need for an operator to go to a remote location to make calibration adjustments.

In view of the foregoing, it will be seen that one aspect of the present invention is to provide an opacity monitor that is easily and readily calibrated.

Another aspect of the present invention is to provide an opacity monitor which has calibration means incorporated therein and which does not require any auxiliary equipment to effect calibration thereof.

Yet another aspect of the present invention is to provide an opacity monitor that does not require the stopping of the process being monitored to effect calibration thereof.

These and other aspects of the present invention will be more clearly understood after a review of the following description of the preferred embodiment when considered with the drawings.

DESCRIPTION OF THE PREFERRED EMBODIMENT

Figure 1:
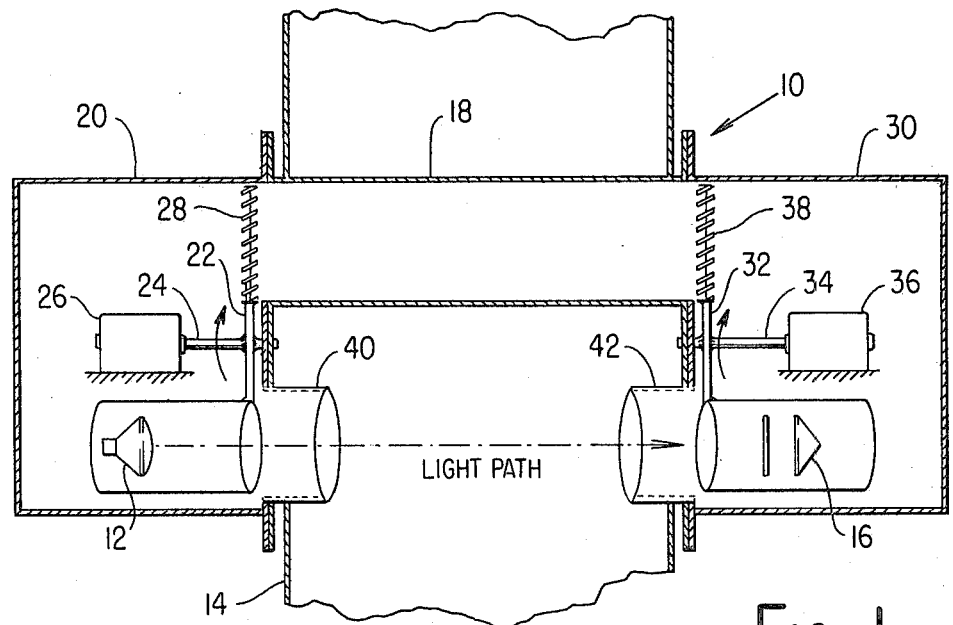
FIG. 1 is a schematic representation of an opacity monitor constructed in accordance with the present invention.

Referring now to the drawings where the illustrations are for the purpose of describing the preferred embodiment of the invention and are not intended to limit the invention hereto, FIG. 1 illustrates a transmissometer 10 comprising a light source 12 mounted on one side of a duct 14, a detector 16 mounted on the opposite side of the duct 14, and a calibration pipe 18 extending through the duct.

The light source 12 is mounted within a first housing 20 attached to the duct 14. As shown schematically in FIG. 1, the light source 12 is mounted on a first plate 22 fixed to the output shaft 24 of a first motor 26 mounted to the housing 20. A shutter 28 is also mounted on the plate 22 and is displaced 180° from the light source 12.

The detector 16, which is typically a photo-electric eye, is mounted within a second housing 30 attached to the duct 14 opposite the light source 12. The detector 16 is mounted on a second plate 32 fixed to the output shaft 34 of a second motor 36 mounted to the housing 30. A shutter 38 is also mounted on the plate 32 and is displaced 180° from the detector 16.

A first light tube 40 extends from the first housing 20 and through one wall of the duct 14 and is in alignment with a similar, second light tube 42 which extends from the second housing 30 and through an opposing wall of the duct 14. The calibration pipe 18 extends between the first and second housing 20 and 30, and through the duct 14, and is aligned within the duct with the light tubes 40 and 42 along the gas flow path through the duct.

The motors 26 and 36 can be servo motors, rotary solenoids, or the like which can be controlled so that for each actuation thereof their output shafts rotate 180° between a first position wherein the plates 22 and 32 are positioned to align the light source 12 and the detector 16 with the light tubes 40 and 42, and thus in mutual alignment across the duct 14, and a second position wherein the light source 12 and the detector 16 are aligned across the calibration pipe 18. When the light source 12 and the detector 16 are aligned with the light tubes 40 and 42, the shutters 28 and 38 are aligned with the calibration pipe 18, and when the light source 12 and the detector 16 are aligned with the calibration pipe 18, the shutters 28 and 38 are aligned with the light tubes 40 and 42.

Figure 2:
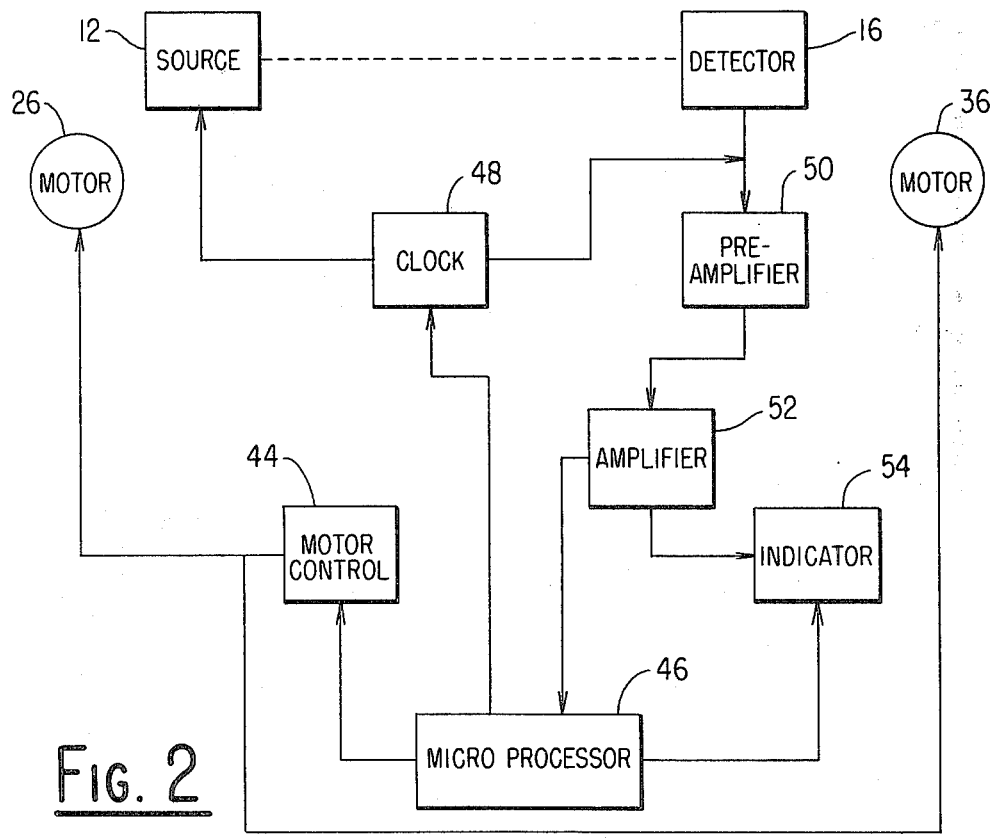
FIG. 2 is a schematic diagram of an opacity monitoring system incorporating the present invention.

A schematic representation of an opacity monitoring system incorporating the present invention is illustrated in FIG. 2. The light source 12 and the detector 16 are driven, by means of the plates 22 and 32, by motors 26 and 36, respectively. The motors are controlled in unison by a motor control circuit 44 which is responsive to gating signals produced by a microprocessor 46. In accordance with a predetermined program contained within the microprocessor 46, the motors 26 and 36 rotate the light source 12 and the detector 16, respectively, at selected times to effect the zero and calibration procedures.

A clock 48 controls the electrical pulses to the light source 12 and also gates the output of the detector 16 so that the electrical pulses from the detector 16 to a preamplifier 50 are synchronized with the energization of the light source 12. This prevents the detection of false signals generated by ambient light, such as direct or reflected sunlight. Electrical signals from the preamplifier 50, which is physically located at the detector 16, are then transmitted to an amplifier 52 where the signals are conditioned and reconstructed for transmission to an indicator 54, such as a meter, digital display, chart recorder or the like.

The amplified signals are also transmitted to the microprocessor 46 where they are further conditioned and manipulated mathematically to compensate for different stack exit cross-sections, signal averaging, and for providing appropriate alarm signals.

In operation, when an opacity measurement is to be taken, the light source 12 and the detector 16 are first rotated to the second position wherein they are aligned with the calibration pipe 18 so that a true zero reading and accurate calibration can be obtained. Once the zero reading and calibration are obtained, the light source 12 and the detector 16 are rotated to their first position in alignment with the light tubes 40 and 42 across the duct 14 so that an opacity measurement can be taken on the gases flowing through the duct, as described above.

Certain modifications and improvements will occur to those skilled in the art upon reading the foregoing description. It will be understood that all such improvements and modifications have been deleted herein for the sake of conciseness and readability but are properly within the scope of the following claims.

We claim:

1. In an opacity monitoring system comprising a light source mounted on one side of a duct, a detector mounted on the opposite side of the duct, and means defining an open light path across said duct between said light source and said detector, a calibration tube extending across said duct and closed to the interior of said duct, means mounting said light source for rotation about a first axis substantially perpendicular to the direction of flow through said duct, means mounting said detector for rotation about a second axis substantially perpendicular to the direction of flow through said duct, means for rotating said light source about said first axis from a first position aligned with said calibration tube, means for rotating said detector about said second axis from a first position aligned with said light path to a second position aligned with said calibration tube, first motor means for rotating said light source about said first axis, second motor means for rotating said detector about said second axis, and control means electrically connected to said first and second motor means and operable to energize said first and second motor means to rotate said light source and said detector in unison.

2. The apparatus as defined in claim 1 wherein said light source is mounted in a first housing attached to one side of said duct, said detector is mounted in a second housing attached to the opposite side of said duct, including a first light tube attached to said first housing and opening into said duct, and a second light tube attached to said second housing and opening into said duct, said first and second light tubes defining said light path.

3. The apparatus as defined in claim 2 including first mounting plate means mounting said light source on an output member of said first motor means for rotation therewith, and second mounting plate means mounting said detector on an output member of said second motor means for rotation therewith.

4. The apparatus as defined in claim 3 including first shutter means attached to said first mounting plate means, wherein said first shutter means is aligned with said calibration tube when said light source is aligned with said first light tube, and wherein said second shutter means is aligned with said first light tube when said light source is aligned with said calibration tube.

5. The apparatus as defined in claim 4 including second shutter means attached to said second mounting plate means, wherein said second shutter means is aligned with said calibration tube when said detector is aligned with said second light tube, and wherein said second shutter means is aligned with said second light tube when said detector is aligned with said calibration tube.

* * * * *